United States Patent
Colborn (10) Patent No.: US 9,220,910 B2
(45) Date of Patent: Dec. 29, 2015

(54) SEIZURE DETECTION USING COORDINATE DATA

(71) Applicant: CYBERONICS, INC., Houston, TX (US)

(72) Inventor: John C. Colborn, League City, TX (US)

(73) Assignee: CYBERONICS, INC., Houston, TX (US)

(*) Notice: Subject to any disclaimer, the term of this patent is extended or adjusted under 35 U.S.C. 154(b) by 76 days.

(21) Appl. No.: 14/149,409

(22) Filed: Jan. 7, 2014

(65) Prior Publication Data

US 2014/0121723 A1    May 1, 2014

Related U.S. Application Data

(63) Continuation of application No. 12/847,922, filed on Jul. 30, 2010, now Pat. No. 8,641,646.

(51) Int. Cl.
| | |
|---|---|
| *A61B 5/00* | (2006.01) |
| *A61N 1/372* | (2006.01) |
| *A61B 5/0245* | (2006.01) |
| *A61B 5/11* | (2006.01) |
| *A61N 1/36* | (2006.01) |

(Continued)

(52) U.S. Cl.
CPC ......... *A61N 1/37252* (2013.01); *A61B 5/0245* (2013.01); *A61B 5/1112* (2013.01); *A61B 5/1118* (2013.01); *A61B 5/4094* (2013.01); *A61B 5/4836* (2013.01); *A61N 1/36064* (2013.01); *A61N 1/36139* (2013.01); *A61N 1/37282* (2013.01); *G06F 19/3418* (2013.01); *A61B 5/002* (2013.01); *A61B 5/0215* (2013.01); *A61B 5/053* (2013.01); *A61B 5/1116* (2013.01); *A61B 5/6833* (2013.01); *A61B 5/6847* (2013.01); *A61B 2562/0219* (2013.01); *A61B 2562/0247* (2013.01); *A61N 1/36114* (2013.01); *G06F 19/345* (2013.01)

(58) Field of Classification Search
CPC .... A61B 5/053; A61B 5/0006; A61B 5/0024; A61B 5/046; A61B 5/0464; A61B 5/0468; A61B 5/0452; A61B 5/0245; A61N 1/37252
See application file for complete search history.

(56) References Cited

U.S. PATENT DOCUMENTS

| | | | |
|---|---|---|---|
| 4,172,459 | A | 10/1979 | Hepp |
| 4,197,856 | A | 4/1980 | Northrop |

(Continued)

FOREIGN PATENT DOCUMENTS

| | | |
|---|---|---|
| EP | 1145736 | 10/2001 |
| EP | 1486232 | 12/2004 |

(Continued)

OTHER PUBLICATIONS

Bachman, D.,S. et al.; "Effects of Vagal Volleys and Serotonin on Units of Cingulate Cortex in Monkeys;" Brain Research, vol. 130 (1977). pp. 253-269.

(Continued)

*Primary Examiner* — Max Hindenburg
(74) *Attorney, Agent, or Firm* — Cyberonics, Inc.

(57) ABSTRACT

A seizure detection device includes a coordinate data interface configured to receive coordinate data for a human, a memory to store coordinate data for a defined location of the human, and a seizure detector configured to identify a seizure event responsive to the coordinate data.

20 Claims, 5 Drawing Sheets

(51) Int. Cl.
*G06F 19/00* (2011.01)
*A61B 5/053* (2006.01)
*A61B 5/0215* (2006.01)

(56) References Cited

U.S. PATENT DOCUMENTS

| | | |
|---|---|---|
| 4,291,699 A | 9/1981 | Geddes et al. |
| 4,320,766 A | 3/1982 | Alihanka et al. |
| 4,541,432 A | 9/1985 | Molina-Negro et al. |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 4,979,511 A | 12/1990 | Terry, Jr. |
| 5,025,807 A | 6/1991 | Zabara |
| 5,062,169 A | 11/1991 | Kennedy et al. |
| 5,113,869 A | 5/1992 | Nappholz et al. |
| 5,137,020 A | 8/1992 | Wayne et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,194,847 A | 3/1993 | Taylor et al. |
| 5,203,326 A | 4/1993 | Collins |
| 5,205,285 A | 4/1993 | Baker, Jr. |
| 5,213,568 A | 5/1993 | Lattin et al. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,243,980 A | 9/1993 | Mehra |
| 5,251,634 A | 10/1993 | Weinberg |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,313,953 A | 5/1994 | Yomtov et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,404,877 A | 4/1995 | Nolan et al. |
| 5,425,373 A | 6/1995 | Causey, III |
| 5,513,649 A | 5/1996 | Gevins et al. |
| 5,522,862 A | 6/1996 | Testerman et al. |
| 5,523,742 A | 6/1996 | Simkins et al. |
| 5,540,730 A | 7/1996 | Terry, Jr. et al. |
| 5,540,734 A | 7/1996 | Zabara |
| 5,571,150 A | 11/1996 | Wernicke et al. |
| 5,610,590 A | 3/1997 | Johnson et al. |
| 5,611,350 A | 3/1997 | John |
| 5,645,077 A | 7/1997 | Foxlin |
| 5,645,570 A | 7/1997 | Corbucci |
| 5,651,378 A | 7/1997 | Matheny et al. |
| 5,658,318 A | 8/1997 | Stroetmann et al. |
| 5,683,422 A | 11/1997 | Rise |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,716,377 A | 2/1998 | Rise et al. |
| 5,720,771 A | 2/1998 | Snell |
| 5,743,860 A | 4/1998 | Hively et al. |
| 5,748,113 A | 5/1998 | Torch |
| 5,792,186 A | 8/1998 | Rise |
| 5,800,474 A | 9/1998 | Benabid et al. |
| 5,807,284 A | 9/1998 | Foxlin |
| 5,808,552 A | 9/1998 | Wiley et al. |
| 5,833,709 A | 11/1998 | Rise et al. |
| 5,853,005 A | 12/1998 | Scanlon |
| 5,879,309 A | 3/1999 | Johnson et al. |
| 5,905,436 A | 5/1999 | Dwight et al. |
| 5,913,876 A | 6/1999 | Taylor et al. |
| 5,916,181 A | 6/1999 | Socci et al. |
| 5,916,239 A | 6/1999 | Geddes et al. |
| 5,928,272 A | 7/1999 | Adkins et al. |
| 5,941,906 A | 8/1999 | Barreras, Sr. et al. |
| 5,942,979 A | 8/1999 | Luppino |
| 5,978,702 A | 11/1999 | Ward et al. |
| 5,978,972 A | 11/1999 | Stewart et al. |
| 5,987,352 A | 11/1999 | Klein et al. |
| 5,995,868 A | 11/1999 | Osorio et al. |
| 6,016,449 A | 1/2000 | Fischell et al. |
| 6,018,682 A | 1/2000 | Rise |
| 6,048,324 A | 4/2000 | Socci et al. |
| 6,061,593 A | 5/2000 | Fischell et al. |
| 6,073,048 A | 6/2000 | Kieval et al. |
| 6,083,249 A | 7/2000 | Familoni |
| 6,091,992 A | 7/2000 | Bourgeois et al. |
| 6,095,991 A | 8/2000 | Krausman et al. |
| 6,104,956 A | 8/2000 | Naritoku et al. |
| 6,115,628 A | 9/2000 | Stadler et al. |
| 6,115,630 A | 9/2000 | Stadler et al. |
| 6,128,538 A | 10/2000 | Fischell et al. |
| 6,134,474 A | 10/2000 | Fischell et al. |
| 6,162,191 A | 12/2000 | Foxlin |
| 6,163,281 A | 12/2000 | Torch |
| 6,167,311 A | 12/2000 | Rezai |
| 6,171,239 B1 | 1/2001 | Humphrey |
| 6,175,764 B1 | 1/2001 | Loeb et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,246,344 B1 | 6/2001 | Torch |
| 6,248,080 B1 | 6/2001 | Miesel et al. |
| 6,253,109 B1 | 6/2001 | Gielen |
| 6,269,270 B1 | 7/2001 | Boveja |
| 6,272,379 B1 | 8/2001 | Fischell et al. |
| 6,304,775 B1 | 10/2001 | Iasemidis et al. |
| 6,315,740 B1 | 11/2001 | Singh |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,361,507 B1 | 3/2002 | Foxlin |
| 6,361,508 B1 | 3/2002 | Johnson et al. |
| 6,366,813 B1 | 4/2002 | DiLorenzo |
| 6,366,814 B1 | 4/2002 | Boveja |
| 6,374,140 B1 | 4/2002 | Rise |
| 6,397,100 B2 | 5/2002 | Stadler et al. |
| 6,427,086 B1 | 7/2002 | Fischell et al. |
| 6,429,217 B1 | 8/2002 | Puskas |
| 6,441,731 B1 | 8/2002 | Hess |
| 6,449,512 B1 | 9/2002 | Boveja |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,501,983 B1 | 12/2002 | Natarajan et al. |
| 6,505,074 B2 | 1/2003 | Boveja et al. |
| 6,532,388 B1 | 3/2003 | Hill et al. |
| 6,539,263 B1 | 3/2003 | Schiff et al. |
| 6,542,081 B2 | 4/2003 | Torch |
| 6,542,774 B2 | 4/2003 | Hill et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,599,250 B2 | 7/2003 | Webb et al. |

(56) References Cited

U.S. PATENT DOCUMENTS

| | | |
|---|---|---|
| 6,609,025 B2 | 8/2003 | Barrett et al. |
| 6,610,713 B2 | 8/2003 | Tracey |
| 6,611,715 B1 | 8/2003 | Boveja |
| 6,611,783 B2 | 8/2003 | Kelly, Jr. et al. |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,985 B2 | 9/2003 | Sweeney et al. |
| 6,628,987 B1 | 9/2003 | Hill et al. |
| 6,629,990 B2 | 10/2003 | Putz et al. |
| 6,647,296 B2 | 11/2003 | Fischell et al. |
| 6,656,125 B2 | 12/2003 | Misczynski et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,721,603 B2 | 4/2004 | Zabara et al. |
| 6,730,047 B2 | 5/2004 | Socci et al. |
| 6,735,474 B1 | 5/2004 | Loeb et al. |
| 6,738,671 B2 | 5/2004 | Christophersom et al. |
| 6,760,626 B1 | 7/2004 | Boveja |
| 6,763,256 B2 | 7/2004 | Kimball et al. |
| 6,768,969 B1 | 7/2004 | Nikitin et al. |
| 6,786,877 B2 | 9/2004 | Foxlin |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,850,601 B2 | 2/2005 | Jones et al. |
| 6,879,850 B2 | 4/2005 | Kimball |
| 6,885,888 B2 | 4/2005 | Rezai |
| 6,904,390 B2 | 6/2005 | Nikitin et al. |
| 6,920,357 B2 | 7/2005 | Osorio et al. |
| 6,923,784 B2 | 8/2005 | Stein |
| 6,931,274 B2 | 8/2005 | Williams et al. |
| 6,934,580 B1 | 8/2005 | Osorio et al. |
| 6,934,585 B1 | 8/2005 | Schloss |
| 6,944,501 B1 | 9/2005 | Pless |
| 6,957,107 B2 | 10/2005 | Rogers |
| 6,961,618 B2 | 11/2005 | Osorio et al. |
| 6,984,993 B2 | 1/2006 | Ariav |
| 6,985,771 B2 | 1/2006 | Fischell et al. |
| 6,990,377 B2 | 1/2006 | Gliner et al. |
| 7,006,859 B1 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,035,684 B2 | 4/2006 | Lee |
| 7,054,792 B2 | 5/2006 | Frei et al. |
| 7,058,453 B2 | 6/2006 | Nelson et al. |
| 7,068,842 B2 | 6/2006 | Liang et al. |
| 7,076,288 B2 | 7/2006 | Skinner |
| 7,077,810 B2 | 7/2006 | Lange et al. |
| 7,079,977 B2 | 7/2006 | Osorio et al. |
| 7,104,947 B2 | 9/2006 | Riehl et al. |
| 7,110,820 B2 | 9/2006 | Tcheng et al. |
| 7,112,319 B2 | 9/2006 | Broderick et al. |
| 7,127,370 B2 | 10/2006 | Kelly et al. |
| 7,134,996 B2 | 11/2006 | Bardy |
| 7,139,677 B2 | 11/2006 | Hively et al. |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,743 B2 | 1/2007 | Heruth et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| RE39,539 E | 4/2007 | Torch |
| 7,204,833 B1 | 4/2007 | Osorio et al. |
| 7,209,786 B2 | 4/2007 | Brockway |
| 7,209,787 B2 | 4/2007 | DiLorenzo |
| 7,221,981 B2 | 5/2007 | Gliner |
| 7,228,167 B2 | 6/2007 | Kara et al. |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,274,298 B2 | 9/2007 | Frank |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,304,580 B2 | 12/2007 | Sullivan et al. |
| 7,305,268 B2 | 12/2007 | Gliner et al. |
| 7,313,440 B2 | 12/2007 | Miesel |
| 7,314,451 B2 | 1/2008 | Halperin et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,330,760 B2 | 2/2008 | Heruth et al. |
| 7,346,391 B1 | 3/2008 | Osorio et al. |
| 7,353,063 B2 | 4/2008 | Simms, Jr. |
| 7,353,064 B2 | 4/2008 | Gliner et al. |
| 7,373,199 B2 | 5/2008 | Sackellares et al. |
| 7,385,443 B1 | 6/2008 | Denison |
| 7,389,144 B1 | 6/2008 | Osorio et al. |
| 7,389,147 B2 | 6/2008 | Wahlstrand et al. |
| 7,395,113 B2 | 7/2008 | Heruth et al. |
| 7,401,008 B2 | 7/2008 | Frei et al. |
| 7,403,820 B2 | 7/2008 | DiLorenzo |
| 7,420,472 B2 | 9/2008 | Tran |
| 7,433,732 B1 | 10/2008 | Carney et al. |
| 7,447,545 B2 | 11/2008 | Heruth et al. |
| 7,454,245 B2 | 11/2008 | Armstrong et al. |
| 7,488,293 B2 | 2/2009 | Marcovecchio et al. |
| 7,488,294 B2 | 2/2009 | Torch |
| 7,491,181 B2 | 2/2009 | Heruth et al. |
| 7,494,464 B2 | 2/2009 | Rzesnitzek et al. |
| 7,502,643 B2 | 3/2009 | Farringdon et al. |
| 7,515,054 B2 | 4/2009 | Torch |
| 7,539,532 B2 | 5/2009 | Tran |
| 7,539,533 B2 | 5/2009 | Tran |
| 7,539,543 B2 | 5/2009 | Schiff et al. |
| 7,558,622 B2 | 7/2009 | Tran |
| 7,565,132 B2 | 7/2009 | Ben |
| 7,590,453 B2 | 9/2009 | Heruth et al. |
| 7,620,456 B2 | 11/2009 | Gliner et al. |
| 7,629,890 B2 | 12/2009 | Sullivan et al. |
| 7,643,655 B2 | 1/2010 | Liang et al. |
| 7,647,121 B2 | 1/2010 | Wahlstrand et al. |
| 7,658,112 B2 | 2/2010 | Nakamura |
| 7,666,151 B2 | 2/2010 | Sullivan et al. |
| 7,714,757 B2 | 5/2010 | Denison et al. |
| 7,717,848 B2 | 5/2010 | Heruth et al. |
| RE41,376 E | 6/2010 | Torch |
| 7,733,224 B2 | 6/2010 | Tran |
| 7,747,318 B2 | 6/2010 | John et al. |
| 7,769,464 B2 | 8/2010 | Gerber et al. |
| 7,775,993 B2 | 8/2010 | Heruth et al. |
| 7,787,946 B2 * | 8/2010 | Stahmann et al. ................ 607/3 |
| 7,792,583 B2 | 9/2010 | Miesel et al. |
| 7,801,603 B2 | 9/2010 | Westlund et al. |
| 7,801,618 B2 | 9/2010 | Pless |
| 7,801,743 B2 | 9/2010 | Graves et al. |
| 7,813,802 B2 | 10/2010 | Tcheng et al. |
| 7,822,481 B2 | 10/2010 | Gerber et al. |
| 7,827,011 B2 | 11/2010 | DeVaul et al. |
| 7,831,305 B2 | 11/2010 | Gliner |
| 7,847,628 B2 | 12/2010 | Denison |

(56) References Cited

U.S. PATENT DOCUMENTS

| | | |
|---|---|---|
| 7,866,212 B2 | 1/2011 | Ariav et al. |
| 7,899,545 B2 | 3/2011 | John |
| 7,935,076 B2 | 5/2011 | Estes et al. |
| RE42,471 E | 6/2011 | Torch |
| 7,957,809 B2 | 6/2011 | Bourget et al. |
| 7,965,833 B2 | 6/2011 | Meir et al. |
| 7,974,671 B2 | 7/2011 | Fujiwara et al. |
| 7,996,076 B2 | 8/2011 | Burns et al. |
| 7,999,857 B2 | 8/2011 | Bunn et al. |
| 8,000,789 B2 | 8/2011 | Denison et al. |
| 8,000,794 B2 | 8/2011 | Lozano |
| 8,021,299 B2 | 9/2011 | Miesel et al. |
| 8,027,730 B2 | 9/2011 | John et al. |
| 8,027,737 B2 | 9/2011 | Kokones et al. |
| 8,075,499 B2 | 12/2011 | Nathan et al. |
| 8,108,033 B2 * | 1/2012 | Drew et al. ............ 600/509 |
| 8,109,891 B2 | 2/2012 | Kramer et al. |
| 2001/0032059 A1 | 10/2001 | Kelly et al. |
| 2002/0072782 A1 | 6/2002 | Osorio et al. |
| 2002/0099417 A1 | 7/2002 | Naritoku et al. |
| 2002/0116030 A1 | 8/2002 | Rezai |
| 2002/0151939 A1 | 10/2002 | Rezai |
| 2002/0188214 A1 | 12/2002 | Misczynski et al. |
| 2003/0040680 A1 | 2/2003 | Hassert et al. |
| 2003/0074032 A1 | 4/2003 | Gliner |
| 2003/0083716 A1 | 5/2003 | Nicolelis et al. |
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0195588 A1 | 10/2003 | Upton et al. |
| 2003/0208212 A1 | 11/2003 | Cigaina |
| 2003/0210147 A1 | 11/2003 | Humbard |
| 2003/0212440 A1 | 11/2003 | Boveja |
| 2003/0236474 A1 | 12/2003 | Singh |
| 2003/0236558 A1 | 12/2003 | Whitehurst et al. |
| 2004/0006278 A1 | 1/2004 | Webb et al. |
| 2004/0030365 A1 | 2/2004 | Rubin et al. |
| 2004/0088024 A1 | 5/2004 | Firlik et al. |
| 2004/0111045 A1 | 6/2004 | Sullivan et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0225335 A1 | 11/2004 | Whitehurst et al. |
| 2004/0249302 A1 | 12/2004 | Donoghue et al. |
| 2004/0249416 A1 | 12/2004 | Yun et al. |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0022606 A1 | 2/2005 | Partin et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060001 A1 | 3/2005 | Singhal et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0107716 A1 | 5/2005 | Eaton et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0192644 A1 | 9/2005 | Boveja et al. |
| 2005/0197590 A1 | 9/2005 | Osorio et al. |
| 2005/0203366 A1 | 9/2005 | Donoghue et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja |
| 2006/0018833 A1 | 1/2006 | Murphy et al. |
| 2006/0074450 A1 | 4/2006 | Boveja |
| 2006/0079936 A1 | 4/2006 | Boveja |
| 2006/0094971 A1 | 5/2006 | Drew |
| 2006/0095081 A1 | 5/2006 | Zhou et al. |
| 2006/0106430 A1 | 5/2006 | Fowler et al. |
| 2006/0135877 A1 | 6/2006 | Giftakis et al. |
| 2006/0135881 A1 | 6/2006 | Giftakis et al. |
| 2006/0149139 A1 | 7/2006 | Bonmassar et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0212097 A1 | 9/2006 | Varadan et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo et al. |
| 2007/0027486 A1 | 2/2007 | Armstrong et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073355 A1 | 3/2007 | DiLorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | DiLorenzo |
| 2007/0142873 A1 | 6/2007 | Esteller et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |

(56) References Cited

U.S. PATENT DOCUMENTS

| | | |
|---|---|---|
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0239210 A1 | 10/2007 | Libbus et al. |
| 2007/0242661 A1 | 10/2007 | Tran et al. |
| 2007/0244407 A1 | 10/2007 | Osorio |
| 2007/0249953 A1 | 10/2007 | Osorio et al. |
| 2007/0249954 A1 | 10/2007 | Virag et al. |
| 2007/0255147 A1 | 11/2007 | Drew et al. |
| 2007/0255155 A1 | 11/2007 | Drew et al. |
| 2007/0260147 A1 | 11/2007 | Giftakis et al. |
| 2007/0260289 A1 | 11/2007 | Giftakis et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2008/0004904 A1 | 1/2008 | Tran et al. |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081958 A1 | 4/2008 | Denison et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0208013 A1 | 8/2008 | Zhang et al. |
| 2008/0208284 A1 | 8/2008 | Rezai et al. |
| 2008/0258907 A1 | 10/2008 | Kalpaxis et al. |
| 2008/0269579 A1 | 10/2008 | Schiebler et al. |
| 2008/0275327 A1 | 11/2008 | Faarbaek et al. |
| 2008/0275328 A1 | 11/2008 | Jones et al. |
| 2008/0275349 A1 | 11/2008 | Halperin et al. |
| 2008/0281376 A1 | 11/2008 | Gerber et al. |
| 2008/0281381 A1 | 11/2008 | Gerber et al. |
| 2008/0281550 A1 | 11/2008 | Hogle et al. |
| 2008/0319281 A1 | 12/2008 | Aarts et al. |
| 2009/0030345 A1 | 1/2009 | Bonnet et al. |
| 2009/0040052 A1 | 2/2009 | Cameron et al. |
| 2009/0054737 A1 | 2/2009 | Magar et al. |
| 2009/0054742 A1 | 2/2009 | Kaminska et al. |
| 2009/0060287 A1 | 3/2009 | Hyde et al. |
| 2009/0076350 A1 | 3/2009 | Bly et al. |
| 2009/0099624 A1 | 4/2009 | Kokones et al. |
| 2009/0099627 A1 | 4/2009 | Molnar et al. |
| 2009/0105785 A1 | 4/2009 | Wei et al. |
| 2009/0137921 A1 | 5/2009 | Kramer et al. |
| 2009/0227882 A1 | 9/2009 | Foo |
| 2009/0227888 A1 | 9/2009 | Salmi |
| 2009/0322540 A1 | 12/2009 | Richardson et al. |
| 2010/0010382 A1 | 1/2010 | Panken |
| 2010/0010392 A1 | 1/2010 | Skelton et al. |
| 2010/0010583 A1 | 1/2010 | Panken et al. |
| 2010/0023348 A1 | 1/2010 | Hardee et al. |
| 2010/0056878 A1 | 3/2010 | Partin et al. |
| 2010/0106217 A1 | 4/2010 | Colborn |
| 2010/0109875 A1 | 5/2010 | Ayon et al. |
| 2010/0121214 A1 | 5/2010 | Giftakis et al. |
| 2010/0217533 A1 | 8/2010 | Nadkarni et al. |
| 2010/0223020 A1 | 9/2010 | Goetz |
| 2010/0228103 A1 | 9/2010 | Schecter |
| 2010/0228314 A1 | 9/2010 | Goetz |
| 2010/0268056 A1 | 10/2010 | Picard et al. |
| 2010/0280336 A1 | 11/2010 | Giftakis et al. |
| 2010/0280578 A1 | 11/2010 | Skelton et al. |
| 2010/0280579 A1 | 11/2010 | Denison et al. |
| 2010/0286567 A1 | 11/2010 | Wolfe et al. |
| 2010/0298661 A1 | 11/2010 | McCombie et al. |
| 2010/0298742 A1 | 11/2010 | Perlman et al. |
| 2010/0305665 A1 | 12/2010 | Miesel et al. |
| 2010/0312188 A1 | 12/2010 | Robertson et al. |
| 2011/0029044 A1 | 2/2011 | Hyde et al. |
| 2011/0040204 A1 | 2/2011 | Ivorra et al. |
| 2011/0040546 A1 | 2/2011 | Gerber et al. |
| 2011/0060252 A1 | 3/2011 | Simonsen et al. |
| 2011/0066062 A1 | 3/2011 | Banet et al. |
| 2011/0066081 A1 | 3/2011 | Goto et al. |
| 2011/0137372 A1 | 6/2011 | Makous et al. |
| 2011/0172545 A1 | 7/2011 | Grudic et al. |
| 2011/0230730 A1 | 9/2011 | Quigg et al. |
| 2011/0245629 A1 | 10/2011 | Giftakis et al. |
| 2011/0251469 A1 | 10/2011 | Varadan |
| 2011/0270117 A1 | 11/2011 | Warwick et al. |
| 2011/0270134 A1 | 11/2011 | Skelton et al. |
| 2011/0295127 A1 | 12/2011 | Sandler et al. |
| 2011/0306846 A1 | 12/2011 | Osorio |
| 2011/0313484 A1 | 12/2011 | Hincapie et al. |

FOREIGN PATENT DOCUMENTS

| | | |
|---|---|---|
| GB | 2026870 | 2/1980 |
| GB | 2079610 | 1/1982 |
| WO | 00/64336 | 11/2000 |
| WO | 2004/036377 | 4/2004 |
| WO | 2005/007120 | 1/2005 |
| WO | 2005/053788 | 6/2005 |
| WO | 2005/067599 | 7/2005 |
| WO | 2006/050144 | 5/2006 |
| WO | 2006/122148 | 11/2006 |
| WO | 2007/066343 | 6/2007 |
| WO | 2007/072425 | 6/2007 |
| WO | 2007/124126 | 11/2007 |
| WO | 2007/124190 | 11/2007 |
| WO | 2007/124192 | 11/2007 |
| WO | 2007/142523 | 12/2007 |
| WO | 2008/045597 | 4/2008 |

OTHER PUBLICATIONS

Baevsky, R.M. "*Analysis of Heart Rate Variability in Space Medicine*;" Human Physiology, vol. 28, No. 2, (2002); pp. 202-213.

Baevsky, R.M., et al.; "*Autonomic Cardiovascular and Respiratory Control During Prolonged Spaceflights Aboard the International Space Station*;"J. Applied Physiological, vol. 103, (2007) pp. 156-161.

Boon, P., et al.; "*Vagus Nerve Stimulation for Epilepsy, Clinical Efficacy of Programmed and Magnet Stimulation*;" (2001); pp. 93-98.

Boon, Paul, et al.; "*Programmed and Magnet-Induced Vagus Nerve Stimulation for Refractory Epilepsy*;"Journal of Clinical Neurophysiology vol. 18 No. 5; (2001); pp. 402-407.

Borovikova, L.V., et al.; "*Vagus Nerve Stimulation Attenuates the Systemic Inflammatory Response to Endotoxin*;" Letters to Nature; vol. 405; (May 2000); pp. 458-462.

Chakravarthy, N., et al.; "*Controlling Synchronization in a Neuron-Level Population Model*;" International Journal of Neural Systems, vol. 17, No. 2 (2007) pp. 123-138.

Clark, K.B., et al.; "*Posttraining Electrical Stimulation of Vagal Afferents with Concomitant Vagal Efferent Inactivation Enhances Memory Storage Processes in the Rat*;" Neurobiology of Learning and Memory, vol. 70, 364-373 (1998) Art. No. NL983863.

Elmpt, W.J.C., et al.; "*A Model of Heart Rate Changes to Detect Seizures in Severe Epilepsy*" Seizure vol. 15, (2006) pp. 366-375.

Frei, M.G., et al.; "*Left Vagus Nerve Stimulation with the Neurocybernetic Prosthesis Has Complex Effects on Heart Rate and*

(56) References Cited

OTHER PUBLICATIONS on Its Variability in Humans:" Epilepsia, vol. 42, No. 8 (2001); pp. 1007-1016.
George, M.S., et al.; "Vagus Nerve Stimulation: A New Tool for Brain Research and Therapy;"Society of Biological Psychiatry vol. 47 (2000) pp. 287-295.
Henry, Thomas R.; "Therapeutic Mechanisms of Vague Name Stimulation;". Neurology, vol. 59 (Supp 4) (Sep. 2002), pp. S3-S14.
Hallowitz et al., "Effects of Vagal Volleys on Units of Intralaminar and Juxtalaminar Thalamic Nuclei in Monkeys;"Brain Research, vol. 130 (1977), pp. 271-286.
Iasemidis; L.D., et al.; "Dynamical Resetting of the Human Brain at Epilepctic Seizures: Application of Nonlinear Dynamics and Global Optimization Techniques;" IEEE Transactions on Biomedical Engineering, vol. 51, No. 3 (Mar. 2004); pp. 493-506.
Iasemidis; L.D., et al.; "Spatiotemporal Transition to Epileptic Seizures: A Nonlinear Dynamical Analysis of Scalp and Intracranial EEG Recordings;"Spatiotemporal Models in Biological and Artificial Systems; F.L. Silva et al. (Eds.) IOS Press, 1997; pp. 81-88.
Iasemidis, L.D.; "Epileptic Seizure Prediction and Control" IEEE Transactions on Biomedical Engineering, vol. 50, No. 5 (May 2003); pp. 549-558.
Kautzner, J., et al.; "Utility of Short-Term Heart Rate Variability for Prediction of Sudden Cardiac Death After Acute Myocardial Infarction"Acta Univ. Palacki. Olomuc., Fac. Med., vol. 141 (1998) pp. 69-73.
Koenig, S.A., et al.; "Vagus Nerve Stimulation Improves Severely Impaired Heart Rate Variability in a Patient with Lennox-Gastaut-Syndrome" Seizure (2007) ARTICLE IN PRESS—YSEIZ-1305; pp. 1-4.
Koo, B., "EEG Changes With Vagus Nerve Stimulation" Journal of Clinical Neurophysiology, vol. 18 No. 5 (Sep. 2001); pp. 434-441.
Krittayaphong, M.D., et al.; "Heart Rate Variability in Patients with Coronary Artery Disease: Differences in Patients with Higher and Lower Depression Scores" Psychosomatic Medicine vol. 59 (1997) pp. 231-235.
Leutmezer, F., et al.; "Electrocardiographic Changes at the Onset of Epileptic Seizures;" Epilepsia, vol. 44, No. 3; (2003); pp. 348-354.
Lewis, M.E., et al.; "Vagus Nerve Stimulation Decreases Left Ventricular Contractility in Vivo in the Human and Pig Heart" The Journal of Physiology vol. 534, No. 2, (2001) pp. 547-552.
Li, M., et al.; "Vagal Nerve Stimulation Markedly Improves Long-Term Survival After Chronic Heart Failure in Rats;" Circulation (Jan. 2004) pp. 120-124.
Licht, C.M.M.; Association Between Major Depressive Disorder and Heart Rate Variability in the Netherlands Study of Depression and Anxiety (NESDA); Arch. Gen Psychiatry, vol. 65, No. 12 (Dec. 2008); pp. 1358-1367.
Lockard et al., "Feasibility and Safety of Vagal Stimulation in Monkey Model;" Epilepsia, vol. 31 (Supp. 2) (1990), pp. S20-S26.
McClintock, P., "Can Noise Actually Boost Brain Power" Physics World Jul. 2002; pp. 20-21.
Mori, T., et al.; "Noise-Induced Entrainment and Stochastic Resonance in Human Brain Waves" Physical Review Letters vol. 88, No. 21 (2002); pp. 218101-1-218101-4.
Mormann, F., "Seizure prediction: the long and winding road," Brain 130 (2007), 314-333.
Nouri, M.D.; "Epilepsy and the Autonomic Nervous System" emedicine (updated May 5, 2006); pp. 1-14; http://www.emedicine.com/neuro/topic658.htm.
O'Regan, M.E., et al.; "Abnormalities in Cardiac and Respiratory Function Observed During Seizures in Childhood" Developmental Medicine & Child Neurlogy, vol. 47 (2005) pp. 4-9.
Pathwardhan, R.V., et al., Control of Refractory status epilepticus precipitated by anticonvulasnt withdrawal using left vagal nerve stimulation: a case report, Surgical Neurology 64 (2005) 170-73.
Poddubnaya, E.P., "Complex Estimation of Adaptation Abilities of the Organism in Children Using the Indices of Responsiveness of the Cardiovascular System and Characteristics of EEG" Neurophysiology vol. 38, No. 1 (2006); pp. 63-74.
Rugg-Gunn, F.J., et al.; "Cardiac Arrhythmias in Focal Epilepsy: a Prospective Long-Term Study" www.thelancet.com vol. 364 (2004) pp. 2212-2219.
Sajadieh, A., et al.; "Increased Heart Rate and Reduced Heart-Rte Variability are Associated with Subclinical Inflammation in Middle-Aged and Elderly Subjects with no Apparent Heart Disease" European Heart Journal vol. 25, (2004); pp. 363-370.
Schernthaner, C., et al.; "Autonomic Epilepsy—The Influence of Epileptic Discharges on Heart Rate and Rhythm"The Middle European Journal of Medicine vol. 111, No. 10 (1999) pp. 392-401.
Terry et al.; "The Implantable Neurocybernetic Prosthesis System", Pacing and Clinical Electrophysiology, vol. 14, No. 1 (Jan. 1991), pp. 86-93.
Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.
Umetani, M.D., et al.; "Twenty-Four Hour Time Domain Heart Rate Variability and Heart Rate: Relations to Age and Gender Over Nince Decades"JACC vol. 31, No. 3; (Mar. 1998); pp. 593-601.
Vonck, K., et al. "The Mechanism of Action of Vagus Nerve Stimulation for Refractory Epilepsy—The Current Status", Journal of Neurophysiology, vol. 18 No. 5 (2001), pp. 394-401.
Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.
Zabara, J.; "Neuroinhibition of Xylaine Induced Emesis" Pharmacology & Toxicology, vol. 63 (1988) pp. 70-74.
Zabara, J. "Inhibition of Experimental Seizures in Canines by Repetivie Vagal Stimulation" Epilepsia vol. 33, No. 6 (1992); pp. 1005-1012.
Zabara, J., et al.; "Neural Control of Circulation I"The Physiologist, vol. 28 No. 4 (1985); 1 page.
Zabara, J., et al.; "Neuroinhibition in the Regulation of Emesis" Space Life Sciences, vol. 3 (1972) pp. 282-292.
Osorio, Ivan et al., "An Introduction to Contingent (Closed-Loop) Brain Electrical Stimulation for Seizure Blockage, to Ultra-Short-Term Clinical Trials, and to Multidimensional Statistical Analysis of Therapeutic Efficacy," Journal of Clinical Neurophysiology, vol. 18, No. 6, pp. 533-544, 2001.
Osorio, Ivan et al., "Automated Seizure Abatement in Humans Using Electrical Stimulation," Annals of Neurology, vol. 57, No. 2, pp. 258-268, 2005.
Sunderam, Sridhar et al., "Vagal and Sciatic Nerve Stimulation Have Complex, Time-Dependent Effects on Chemically-Induced Seizures: a Controlled Study," Brain Research, vol. 918, pp. 60-66, 2001.
Weil, Sabine et al, "Heart Rate Increase in Otherwise Subclinical Seizures is Different in Temporal Versus Extratemporal Seizure Onset: Support for Temporal Lobe Automatic Influence," Epileptic Disord., vol. 7, No. 3, Sep. 2005, pp. 199-204.
Digenarro, Giancarlo et al., "Ictal Heart Rate Increase Precedes EEG Discharge in Drug-Resistant Mesial Temporal Lobe Seizures," Clinical Neurophysiology, No. 115, 2004, pp. 1169-1177.
Zijlmans, Maeike et al., "Heart Rate Changes and ECG Abnormalities During Epileptic Seizures: Prevalence and Definition of an Objective Clinical Sign," Epilepsia, vol. 43, No. 8, 2002, pp. 847-854.
O'Donovan, Cormac A. et al., "Computerized Seizure Detection Based on Heart Rate Changes," abstract of AES Proceedings, Epilepsia, vol. 36, Suppl. 4, 1995, p. 7.
Robinson, Stephen E et al., "Heart Rate Variability Changes as Predictor of Response to Vagal Nerve Stimulation Therapy for Epilepsy," abstract of AES Proceedings,Epilepsia, vol. 40, Suppl. 7, 1999, p. 147.
Long, Teresa J. et al., "Effectiveness of Heart Rate Seizure Detection Compared to EEG in an Epilepsy MoitoringUnit (EMU)," abstract of AES Proceedings, Epilepsia, vol. 40, Suppl. 7, 1999, p. 174.

* cited by examiner

SEIZURE DETECTION USING COORDINATE DATA

CROSS-REFERENCE TO RELATED APPLICATION

This application is a continuation application of U.S. patent application Ser. No. 12/847,922, filed Jul. 30, 2010, and is hereby incorporated herein by reference in its entirety.

BACKGROUND OF THE INVENTION

1. Field of the Invention

The present disclosure generally relates to systems and methods for detecting, predicting or logging seizures in a human patient and, optionally, providing a therapy in response thereto. More particularly, the present disclosure relates to a system and methods for detecting physiological changes indicative of a seizure in a patient having an implanted seizure control device, and using coordinate data, such as GPS, to improve seizure detection algorithm specificity.

2. Description of the Related Art

Implantable devices have been developed for delivering targeted nervous stimulation at preprogrammed intervals as a therapy for neurological disorders, such as epileptic seizures. It has been shown that measurable parameters of cardiac activity correlate with epileptic seizure events. Consequently, methods have been developed for recognizing a seizure event by measuring changes in heart rate. One challenge to this methodology is that many reasons exist that can cause a heart rate change, such as physical exertion. Thus, heart rate changes alone can give a misleading indication of a seizure event if the heart rate changes are precipitated by other causes. The present disclosure is directed to overcoming, or at least reducing the effects, of one or more of the issues set forth above.

SUMMARY OF THE INVENTION

It has been recognized that it would be desirable to discriminate heart rate changes associated with a seizure from heart rate changes precipitated by other causes, when determining whether to trigger nervous stimulation for seizure control.

It has also been recognized that information regarding activity or location or position of an individual can help distinguish heart rate changes that accompany a seizure from those that relate to other causes.

In accordance with one aspect thereof, the present disclosure provides a seizure detection device, including a coordinate data interface configured to receive coordinate data for a human, a memory to store coordinate data for a defined location where the human has previously been, and a seizure detector configured to identify a seizure event responsive to the coordinate data.

In accordance with another aspect thereof, the present disclosure provides a system for nerve stimulation, including a pulse generator device suitable for subcutaneous implantation into a human body, and a coordinate data interface configured to receive coordinate data for the human body. A memory is also provided to store coordinate data for a defined location where the human has previously been, and an activation device is configured to activate the pulse generation device responsive to the coordinate data.

In accordance with yet another aspect thereof, the disclosure provides a method for detecting seizures, including the steps of receiving coordinate data for a human body, determining a seizure threshold responsive to the coordinate data, and identifying a seizure event responsive to the seizure threshold.

These and other embodiments of the present application will be discussed more fully in the description. The features, functions, and advantages can be achieved independently in various embodiments of the claimed invention, or may be combined in yet other embodiments.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope as defined by the appended claims.

DESCRIPTION OF ILLUSTRATIVE EMBODIMENTS

Illustrative embodiments are described below as they might be employed in a system for seizure detection using coordinate data. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments will become apparent from consideration of the following description and drawings. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

As used herein, the term "implantable" means a device that can be completely implanted into a human or animal body, with no portions of the apparatus extending outside the body after implantation.

As used herein, the terms "implantable device" and "implantable medical device" or "IMD" mean any type of electrical device that is implantable into a human or animal body, and is configured to monitor or affect a function of the body. Examples of implantable medical devices include cardiac pacemakers, nerve stimulation devices, and implantable drug delivery devices.

There are a variety of implantable devices that can be used for monitoring and affecting physiological or biological function of a human body. Such devices include cardiac pacemakers, implantable drug delivery systems and nerve stimulation devices. Among the latter are implantable devices for nerve stimulation, such as vagus nerve stimulation (VNS). VNS was approved by the FDA in 1998 as an adjunctive therapy for epilepsy with partial onset seizures. VNS is achieved through an implanted pulse generator that delivers a bipolar, biphasic pulse to the vagus nerve. The implant procedure is very similar to the implantation of a pacemaker. The generator is implanted subcutaneously, typically in the upper left pectoral region. An electric lead is connected between the pulse generator and one or more electrodes that are attached to the vagus nerve.

Figure 1:
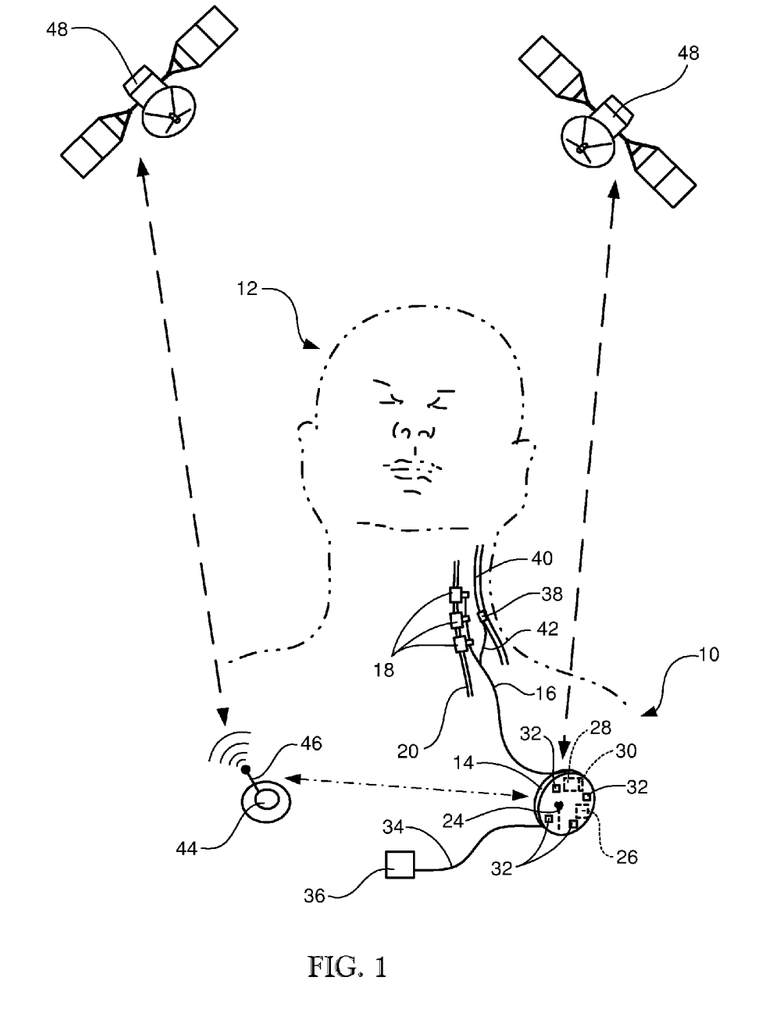
FIG. 1 is a schematic representation of a human subject implanted with an embodiment of a subcutaneous vagus nerve stimulation system, including apparatus for receiving coordinate data of the human subject and identifying a seizure event responsive to the coordinate data.

Shown in FIG. 1 is a schematic diagram of one embodiment of an implantable vagus nerve stimulation system, indicated generally at 10, implanted into a patient 12. The system includes a pulse generator 14, and a tether or lead 16 that has one or more electrodes 18 at its distal end. The tether and electrodes are collectively referred to as the lead, and the lead provides an interface between the pulse generator 14 and the electrodes 18. The electrodes 18 are attachable to the vagus nerve 20. An implantable VNS system of this type and having these basic features is known to those of skill in the art, and is commercially available, such as from Cyberonics, Inc. of Houston, Tex.

The implantable VNS system 10 can also include an antenna 24, a GPS receiver 26, and a microprocessor 28 with digital memory 30. These elements can be included within the housing of the pulse generation device 14. It will be appreciated by those of skill in the art that the pulse generation device can also include other elements that are not shown in FIG. 1, such as a rechargeable battery, etc. for providing electrical power to the device through periodic inductive recharging of the battery. The antenna 24 is a common element for an implantable pulse generation device, and is often provided to send and/or receive data and programming and control instructions from an external communications device, such as a heart monitor patch 44. This allows the implanted device to receive programming and control instructions from the external communications device, and to transmit data regarding operation of the pulse generation device. Communications and control with implanted devices is well known and widely used. Devices such as pacemakers and the like are routinely programmed and/or controlled via wireless communication methods, such as the Medical Information Communication System protocol (MICS), which uses radio waves to transmit information to and from implanted devices.

The pulse generator 14 can be a multi-programmable device, which allows a physician to set various parameters of operation of the device. The programmable parameters can include signal amplitude (e.g., 0-3.5 mA), frequency (e.g., 1-30 Hz), pulse width (e.g., 130-1000 μs), signal ON time (e.g., 7-60 sec) and signal OFF time (e.g., 0.2-180 min). It is to be appreciated that these pulse parameters are only exemplary, and that other parameters can also be used. The pulses can be delivered at the specified amplitude and frequency over the course of the ON time, and then during the OFF time, no stimulation takes place. This type of device typically does not stimulate continuously because it has been found that the antiepileptic effect tends to last much longer than the actual time of stimulation. In one embodiment, pulse settings can be 2 mA, at 15 Hz frequency, 250 μs pulse width, with a 30 sec ON time, and 5 min OFF time. The variability in parameters allows the physician to adjust for greater efficacy or less severe side effects, depending on the patient.

The implantable nerve stimulation device can also include programming and structure to allow adjustment of its operation in real-time based upon detected physiological conditions of the patient in whom it is implanted. Of particular interest in this disclosure, a seizure detector can be provided in conjunction with an implanted device, such as the pulse generation device 14, to identify a seizure event based upon at least one body parameter and coordinate data indicating position or motion of the patient. In one embodiment, the pulse generation device 14 can include a device for detecting the cardiac cycle, as one example of a body parameter or physiological condition of the human subject. There are many different ways to detect cardiac cycles, and several of these are shown in FIG. 1. For example, the implanted pulse generation device 14 can include multiple electrodes 32 on its outer surface or casing (but electrically insulated from the casing), the electrodes being in contact with bodily fluids and thereby detecting a change in electrical potential, which gives an ECG (Electro-CardioGram) signal indicative of the patient's cardiac cycle. As another alternative, another lead 34 can extend from the pulse generation device 14 to a separate implanted heart monitoring device 36, which includes a group of spaced electrodes (not shown) that measure ECG. Such an implanted device can be anchored to a rib or other anatomical structure. As another alternative, a lead with electrodes attached directly to the heart (not shown) can also be used.

As another alternative for monitoring the cardiac cycle of the subject 12, a pressure transducer 38 can be placed next to an artery, such as the carotid artery 40. It is to be appreciated that in the case of vagus nerve stimulation, the carotid artery 40 is relatively close to the vagus nerve 20 in the neck region. Thus, a surgeon could extend a branch 42 of the lead 16 toward the carotid artery during implantation of the nerve stimulation electrodes 18, and implant the pressure transducer 38. This pressure transducer detects changes in pressure adjacent to the artery, which are indicative of the cardiac cycle of the subject.

While the heart monitoring devices discussed above involve implanted structure, it is also to be appreciated that external devices can also be used for monitoring the subject's heart. For example, another method for detecting cardiac cycles can include the use of an external patch 44 which can be adhered to the skin of the chest of the subject 12 and can be similar to current Holter monitors. The patch can include a group of spaced electrodes (not shown), which detect the subject's ECG, in the same manner as implanted electrodes. The use of external adhesive electrodes for measuring the cardiac cycle is widely known in the medical arts. The patch 44 can include internal circuitry and a power source (not shown) and an antenna 46, so that the cardiac cycle information can be wirelessly transmitted to the pulse generation device 14. It is to be understood that, while the patch 44 is shown having an external antenna 46, this is for illustrative purposes only, and does not necessarily represent actual physical structure. It will be appreciated that the antenna can be an internal part of the patch device itself. This sort of patch can be a disposable device, which the subject can wear for a period of time and then replace with a new one whenever desired. The external patch is thus one example of an external communication device that can collect and/or receive seizure event data and threshold parameters associated with physical coordinates of the patient (e.g., GPS data).

It is to be appreciated that other heart monitoring devices, whether implanted or external, can be used in a seizure detection system as disclosed herein. For example, the discussion of the external patch 44 above applies equally to Holter monitors, which come in many varieties and sizes (e.g., simple strap versions commonly used during exercise or a larger "pager style" connected to multiple adhesive electrode patches). Whatever method is used for detecting the subject's cardiac cycle, data regarding the heart rate, heart rate variability, etc. of the subject are continuously transmitted back to the microprocessor 28 of the pulse generator 14. This allows the pulse generation device to be programmed to adjust nerve stimulation based upon the events detected from the cardiac cycle of the subject.

It is known that measurable parameters of cardiac activity correlate with epileptic seizure events. For example, an accelerated heart rate (tachycardia) often accompanies the onset of a seizure event. As used herein, the term "tachycardia" is used in a broader sense than that customarily used by cardiologists—it is used to generally refer to any increase in heart rate. When tachycardia is detected by the microprocessor 28, its programming can cause the pulse generation device to initiate nervous stimulation to treat the seizure. The microprocessor can include activation circuitry that is programmed and configured to activate the implantable device in response to at least one of the coordinate data and the body parameter or body signal data. In this way, the microprocessor 28 of the pulse generation device operates as an activation device for initiating nervous stimulation via the pulse generator. It is believed that nervous stimulation upon detection of a possible seizure can shorten the duration or lessen the severity of a seizure event. Moreover, it is believed that timely nervous stimulation upon first detection of seizure precursor symptoms can even prevent a seizure from fully developing. It is to be understood that to say that the seizure detector merely detects tachycardia can be a simplification. The algorithm for analyzing the cardiac cycle can do more than merely detect an elevated heart rate. Specifically, the algorithm may use matching techniques to identify tachycardia typical of seizures, use accelerometer or other data to confirm or deny seizure detections, or use linear or non-linear properties of heart rate variability (and its derivatives) to detect or categorize seizure events.

One challenge to this methodology is that there are many possible causes for heart rate and cardiac cycle changes, such as physical exertion. The inventor has recognized that it is desirable to discriminate between the causes of cardiac cycle change when determining whether a seizure event has begun, and whether to trigger nerve stimulation for seizure control. The inventor has determined that information regarding an individual's activity or location can help distinguish cardiac cycle changes or other detectable physiological parameters that accompany a seizure from those that relate to other causes. Advantageously, the inventor has developed systems and methods disclosed herein for obtaining and using coordinate data related to the location of the human subject for more accurately identifying seizure events, and for determining a seizure threshold responsive to the coordinate data. In particular, in various embodiments, the apparatus and methods disclosed herein involve the use of GPS (Global Positioning System satellite data) or other coordinate measurement systems for seizure detection and logging specificity improvement.

GPS transceivers have become a common part of many electrical devices. For example, laptop computers, personal digital assistants (PDA's) and many or most smart phones now incorporate a GPS transceiver. The implanted vagus nerve stimulation system shown in FIG. 1 also includes a GPS transceiver 26, which is interconnected to the antenna 24 and the microprocessor 28 and memory 30. The GPS transceiver is one type of coordinate data interface, and is configured to receive coordinate data for the human patient. With these elements, the microprocessor can periodically or continuously determine the subject's location using the publically-accessible GPS satellite system. The coordinate data can then be stored in the memory 30. This data can represent a defined location for the patient. This can be a user-defined location or a previously designated location, for example. The location can also be a mobile location. It is to be appreciated that the defined location is not limited to locations where the patient has been. For example, it can be advantageous to be able to program in, for example, a beach, hunting camp or other area where the patient has not been but intends to go, and where a seizure would present elevated risks of injury to self or others. As is well known, the GPS system allows tracking of latitude, longitude and altitude of the transceiver at any given time, based upon the position of the transceiver 26 relative to multiple GPS satellites 48, and also provides very accurate time data. Moreover, receiving data regarding changes in position over time allows the system (e.g., the microprocessor 28) to also determine velocity and direction of motion of the subject at any time. In other words, the microprocessor can be programmed as a movement calculator, which can determine movement in response to coordinate data over time.

Figure 2:
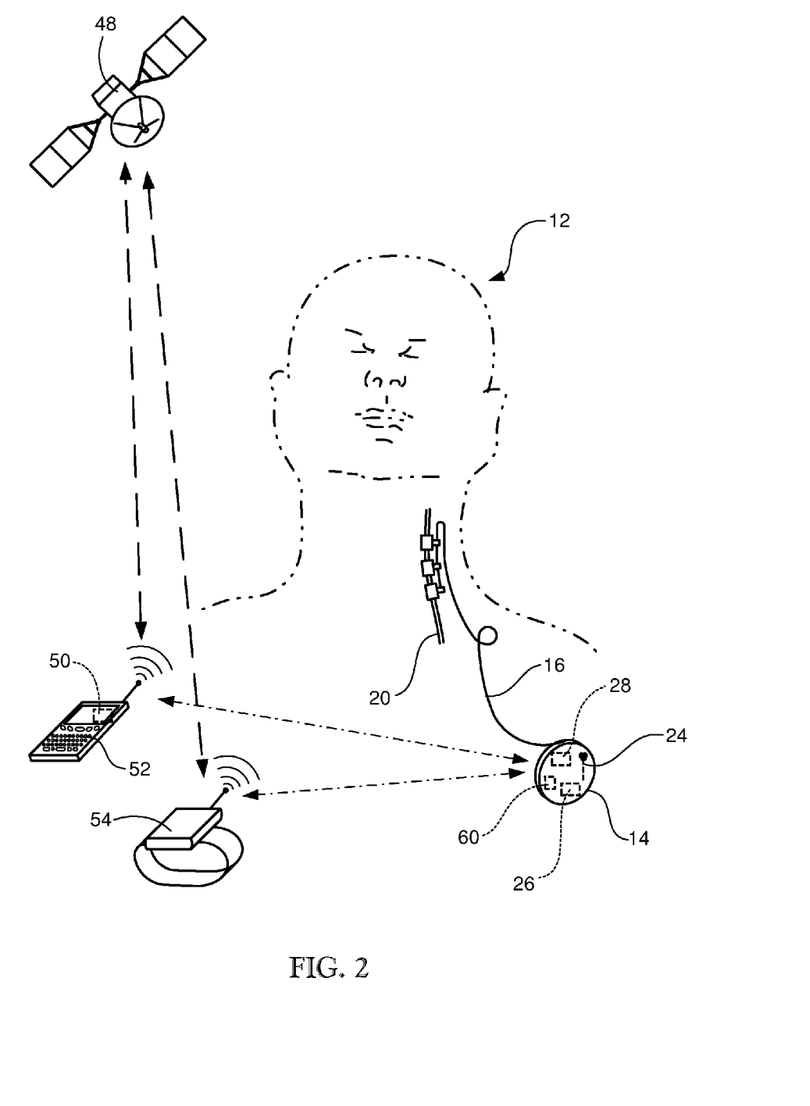
FIG. 2 is a schematic representation of a human subject implanted with another embodiment of a subcutaneous vagus nerve stimulation system, including apparatus for identifying a seizure episode based upon coordinate data associated with a human subject.

While the GPS transceiver 26 is shown incorporated into the implanted pulse generation device in FIG. 1, the GPS transceiver can be placed in other locations associated with the patient's body, such as an external communications device. An external communications device can thus provide the coordinate data interface discussed above, and can function as an activation device for the implanted device. The external communications device can include activation circuitry and programming for activating the implantable device (e.g. via wireless signals) in response to the coordinate data and the body parameter or body signal data. A variety of types of external devices can be used. Some of these are shown in FIG. 2. For example, a GPS transceiver 50 can be incorporated into a smart phone 52 or similar device that is substantially constantly kept in the possession of the person. Alternatively, a wristwatch or wristwatch-like device 54 or other wearable device can include a GPS transceiver which receives locational information and transmits this information wirelessly to the pulse generation device 14. Other wearable or external communication devices can also be used. The smart phone 52 and wristwatch device 54 are shown in FIG. 2 with antennas, which are intended to represent the wireless communications capability of the devices, rather than the shape or position of an actual antenna structure. The antenna allows the external device to receive GPS signals from the satellites 48, and transmit the received GPS data to the pulse generation device 14 using Bluetooth or some other wireless transmission protocol, for example. The wireless external device can be a cellular device, and can house the coordinate data interface and the activation device for the pulse generator. In this way coordinate signals from a wireless external communication device can be transmitted to the pulse generation device. It is recognized that the accuracy of seizure detection can be affected if the GPS device is not kept upon the person of the epileptic patient.

Having the GPS transceiver included within a device other than the pulse generation device 14 can be desirable for power conservation. It will be apparent that power consumption of a GPS transceiver that is in substantially constant communication with the GPS satellite system and a microprocessor that analyzes the positional information can use significant power, which is at a premium with implanted devices. Thus, having an external GPS device can reduce the power demands of the implanted device. Since the external device and the implanted device are presumably kept in relatively close proximity (both upon the person of the epileptic patient), wireless transmission between these devices can be at a much lower power than communication with the GPS system or some other wireless system, thus reducing the power demands upon the implanted device.

Additionally, microprocessing tasks and analysis can be transferred to an external device, rather than being performed by the microprocessor 28 of the pulse generation device, with the results of those microprocessing tasks transmitted to the implanted device. This can also conserve power for the implanted device. For example, the microprocessor associated with a smart phone 52 or wristwatch device 54 or some other external device can be programmed to receive cardiac cycle information (e.g., from an external heart monitoring device or transmitted from the pulse generator 14 or some other implanted device) as well as locational information (GPS, etc.), and perform the analysis discussed herein to distinguish seizure related tachycardia from other causes. The external device can then transmit operational commands or other information to the pulse generation device 14 that can affect its operation, when a seizure event is detected.

Having a GPS transceiver on or associated with the subject 12, along with an implanted or external seizure detector, such as a heart monitoring device, as shown in FIG. 1, allows the system to use location and motion information in conjunction with seizure detection (e.g. heart rate) information to increase confidence in a seizure detection determination. For example, if a heart rate increase accompanies a change in velocity to a fairly constant 3-7 mph, then the system can reduce seizure declaration likelihood (i.e., increase an adaptive threshold), because the change in velocity indicates that the change in heart rate likely results from the person walking or jogging. On the other hand, if no contemporary change in velocity is detected in association with the other seizure detection sensors, then the system can increase the seizure detection likelihood (i.e. reduce the adaptive threshold), so that this heart rate event is considered more likely to accompany a seizure event. This is the basic analytical method for detecting seizures using coordinate data. In this way the seizure detection system is programmed with a threshold evaluator or threshold determining element (i.e. threshold determining logic), which can determine a dynamic seizure detection threshold in response to the coordinate data (representing location and/or motion). Threshold parameters associated with various physical locations or coordinates can be stored in the memory of the seizure detection device (e.g. the implanted device or external communications device).

Figure 5:
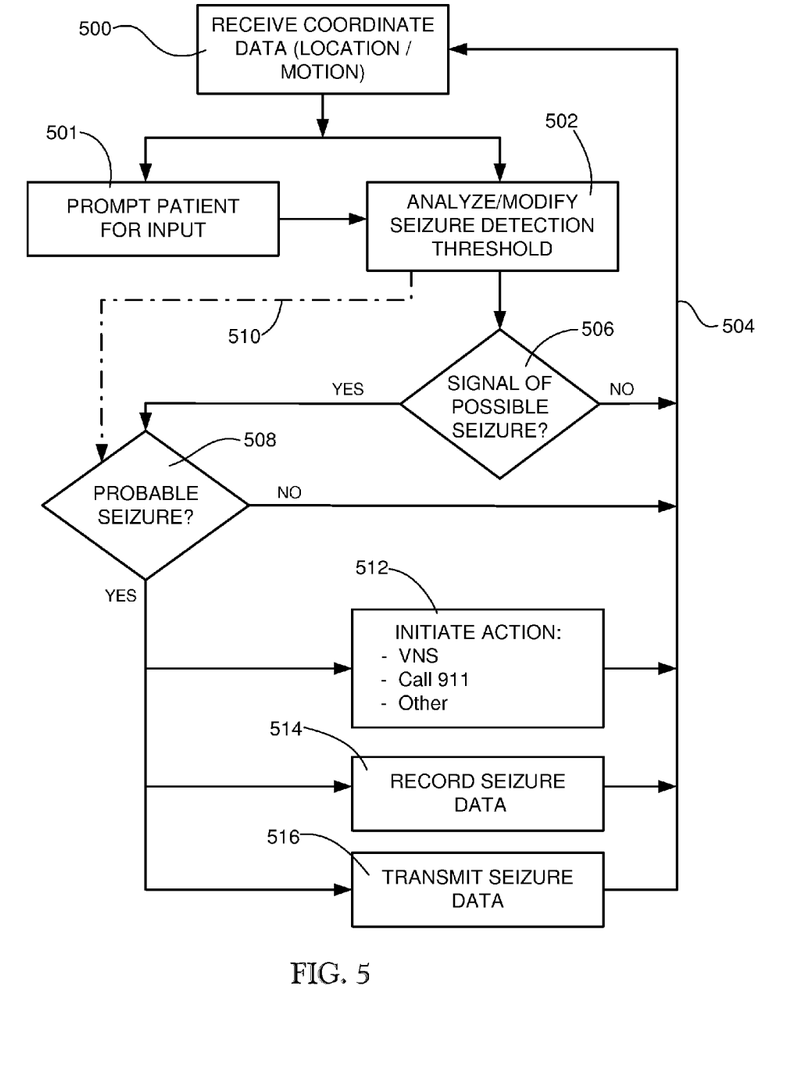
FIG. 5 is a block diagram outlining the steps in an embodiment of a method for determining a seizure threshold and identifying a seizure episode responsive to coordinate data.

A flowchart outlining the basic steps in this method is provided in FIG. 5. The system first receives the coordinate data (step 500), which can be GPS data or some other data. Coordinate data also includes data regarding motion, which can involve time-based analysis of GPS or other positional information in order to determine velocity. In either case, the positional or velocity-related data is referred to herein as coordinate data. Based upon this data, the system analyzes or modifies a seizure detection threshold (step 502) with reference to the patient's location or motion. As shown by return arrow 504, so long as no signal indicating a possible seizure is received by the associated heart monitoring device (step 506), the system simply returns to step 500 and continues to monitor and receive the coordinate data, and periodically adjust the seizure detection threshold as needed (step 502).

However, if a signal indicating a possible seizure (e.g., tachycardia or other signal) is received (at step 506), the system then determines whether a seizure is probably occurring (step 508). This analysis is based upon the modified seizure detection threshold that is part of a seizure detection algorithm, which was determined at step 502, as represented by dashed arrow 510. The difference between analytical steps 506 and 508 is the difference between possible and probable. Step 506 merely determines that a seizure is possible, based upon the received signal. At step 508, it is determined whether a seizure is probable or not, based upon the modified seizure detection threshold. As noted above, once the system has determined, from the coordinate data, how to adjust the seizure detection threshold, its ability to selectively identify a probable seizure is improved. If, in view of the modified seizure detection threshold, it is determined that the detected signal indicating a possible seizure is not likely to be indicative of a seizure, the system can again return to step 500 and continue to monitor and receive the coordinate data, and periodically adjust the seizure detection threshold (step 502). However, if a seizure is detected in view of the modified seizure detection threshold, one or more of various actions can be initiated, as indicated in boxes 512, 514 and 516. These are discussed in more detail below.

Figure 3:
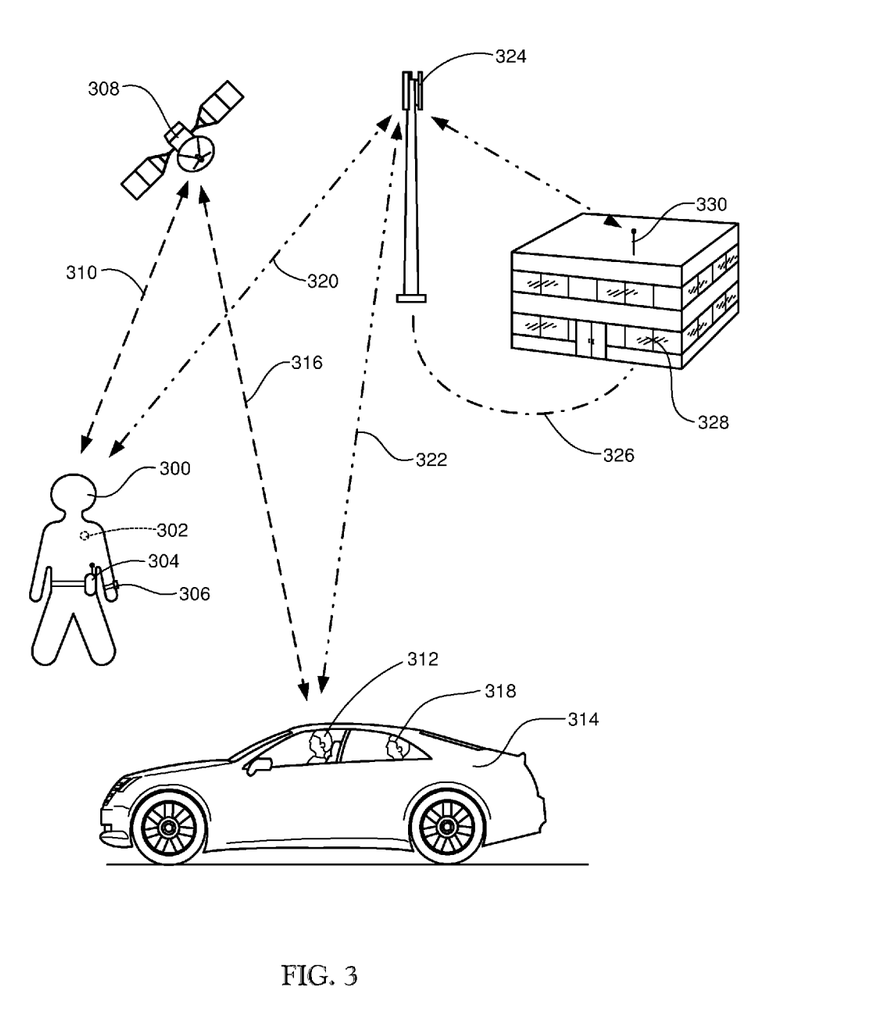
FIG. 3 is a schematic representation of another embodiment of a system for identifying a seizure episode based upon coordinate data associated with a human subject.

The configuration described above allows the system to be used in a variety of ways, some of which are illustrated in FIG. 3. Shown in FIG. 3 is a patient 300 having an implanted VNS device 302, and a smart phone 304 and wristwatch device 306. These external devices are intended to be indicative of any external GPS and/or microprocessor device. It is to be understood that the operational capabilities illustrated in FIG. 3 can be applied whether the implanted device is associated with a coordinate data system like that of FIG. 1 or FIG. 2, or other embodiments. The depiction of the patient 300 is intended to represent the person in any common condition—such as standing, walking, running, etc. Whether through the implanted device 302 or an external device 304, 306 (depending on which device includes a GPS transceiver), the person's position is continually monitored via the GPS satellite system 308, as indicated by dashed line 310. By tracking the person's position over time, the microprocessor that receives the GPS information (like the GPS transceiver, the microprocessor can be part of the implanted pulse generation device 302 or part of an external device 304, 306) can determine the velocity of the person in three dimensions at any time.

Similarly, the microprocessor can incorporate automotive travel logic into the seizure detection algorithm to account for instances when the defined location of the person is mobile. Shown in FIG. 3 is a person 312 in an automobile 314. Though not shown, this person also has a GPS based seizure detection system, like the person 300, and this system is in communication with the satellite based GPS system, as indicated at 316. The microprocessor associated with the seizure detection system can be programmed so that patterns of velocity indicative of automotive travel are recognized and used to modify the seizure detection threshold. Patterns of velocity indicative of automotive travel can include motion at anything above a running speed (e.g., 20 mph), for example. When automotive travel is recognized, the system can adjust (either increase or decrease) the seizure declaration likelihood. On one hand, the system can reduce the adaptive threshold in the circumstance of probable automotive travel because (1) there is less risk of harm from a seizure when traveling as a passenger in a motor vehicle, and (2) there is less likelihood of exertional tachycardia while traveling in a car or bus.

The seizure detection threshold can also vary depending upon the person's relationship to the vehicle—i.e. whether a driver or passenger. For example, tachycardia can be considered more likely for a driver 312, especially in crowded or difficult traffic conditions, than for a passenger 318, as shown in FIG. 3. This sort of factor can come into play in other situations, too. Thus, the seizure detection system disclosed herein can include another feature shown in FIG. 5. In addition to receiving coordinate data (step 500) and modifying the seizure detection threshold based on that information (step 502), the system can also prompt a patient to input relevant locational or conditional information (step 501). For example, when the system detects velocity data indicative of automotive travel, the patient's smart phone or other external device (52 in FIG. 2) can prompt the user with a question such as "Are you traveling in a motor vehicle?" The patient can then enter the appropriate answer to confirm their condition. The system can then ask a follow-up question such as "Are you driving or are you a passenger?"

In this way the coordinate data interface prompts the user to provide information that can identify their location, thus allowing any location to become a user-defined or designated location. In one embodiment, the coordinate data interface can display a predetermined list of location types, from which the user can select to identify the location. For example, the display may list "home", "work", "shopping" and "vehicle" as possible location choices. Multiple nested lists can be involved. When the user selects one, the system can then store the coordinate data of that location in conjunction with the identifier. In another embodiment, the coordinate data interface can be configured to receive an identifying name for the defined location via input of the user or a caretaker or medical personnel, for example. The named location can also have a location type associated with it, such as via a predetermined list of location types, in the manner discussed above.

The system can also prompt for risk factor inputs. These risk factor inputs can then be associated with physical coordinates of a defined location, and can be used to determine the seizure threshold responsive to the risk factor inputs and the coordinate data. The seizure detection algorithm's thresholds can be lowered to be more sensitive to possible seizures when the user is in a risky location. The risk of harm to the user increases in locations such as the gym, swimming pool, bath tub, driver's seat of a vehicle, kitchen, staircase, on a bicycle, and so forth. Each location can have a corresponding risk factor associated with it or the user can input the risk factor necessary for a certain location. The risk factor input can simply be the coordinate data and modify the risk factor dynamically as the user, for example, moves through the house from the bed, to the bath tub, to the kitchen, to the dining room, and then to the vehicle. The user can also input the risk factor by defining a location (e.g., a bicycle) as the user arrives at the location. The user can also input a risk factor without defining the location by, for example, setting a high risk factor when rock climbing and then input a low risk factor when the user eats a picnic lunch near the rock he climbed.

After the user has been prompted to enter relevant information, the system can then adjust the seizure detection threshold. In one embodiment, if a person is a passenger, the seizure detection algorithm can operate normally, but if the person is a driver, the algorithm can become more aggressive (e.g., lowering a threshold) to act upon every possible seizure, for example. Alternatively, the system can use the knowledge that the patient is the driver to separate out tachycardia induced by the stress of driving from tachycardia (or other cardiac cycle events) resulting from seizures.

While much of the above discussion has considered seizure detection based upon sensing tachycardia and cardiac cycles, it is to be understood that this is only one example of a body parameter or physiological condition that can be indicative of a possible seizure event. It is to be appreciated that seizure detection can be accomplished using any one or more of a wide variety of body parameters, in addition to cardiac cycles. For example, seizure detection data can be obtained from cardiovascular signals, respiratory signals, skin signals, pupillary signals, temperature signals, peristaltic signals, brain signals, cranial nerve signals, spinal cord signals, peripheral nerve signals, autonomic nerve or ganglia signals, biomedical presence or concentration signals (i.e. detection of a particular chemical species), body kinetic, position and force signals, and others. Additionally or alternatively, neurological signals, such as those generated by the brain or cranial nerves can be used for detecting a seizure. Exemplary body parameter sensor(s) can include electrocardiography (EKG) devices, accelerometers, inclinometers, pupillometers, face or body temperature monitors, skin resistance monitors, and/or sound and pressure sensors, among others. Those of skill in the art will be aware that sensor(s) to detect these and other body parameters are commercially available, and can be placed in, on, or near a particular organ, tissue, nerve, or blood vessel of the patient, or outside the patient's body, such as on the patient's skin or in the patient's environment.

Referring back to FIG. 3, the system can be configured with additional functionality. As shown by dashed lines 320 and 322, the seizure detection system can incorporate mobile communications technology that allows wireless communication with a cellular phone system (represented by a cell tower 324), which can further connect into the publicly switched telephone system (PSTN) 326. This allows the seizure detection system to communicate with a base station, medical professional, hospital or the like, as represented by building 328, when a seizure is detected. Such remote communications can be desirable for many possible reasons, such as for health monitoring, emergency medical assistance, transmitting seizure related data, providing notifications or programming updates for an implanted device, etc. Various options for action upon detection of a seizure are indicated in FIG. 5, and these can include options that involve remote communications. For example, as indicated in box 512, upon detection of a seizure the system can actuate an implanted nerve stimulation device (14 in FIG. 1) to initiate nervous stimulation. In certain circumstances and certain locations the system can dial 911 to request emergency medical aid. Other actions related to the patient can also be taken.

Additionally, upon detection of a seizure the seizure detection system can begin recording data of the patient and other conditions, perhaps at a faster rate than normally. For example, if the system normally checks position and motion at a rate of once every 4 seconds when no seizure is detected, detection of a seizure could initiate electronic recording of the person's location, movement, heart rate, blood pressure, and other possible factors at a much higher refresh rate—e.g.

every 1 second—during the seizure event. This information can be recorded or logged by the microprocessor (step 514) and/or transmitted to a remote location (step 516) if desired. A remote monitoring location or facility can also include its own wireless communication capability, as indicated by antenna 330, to allow direct communications with seizure detection systems, as opposed to or in addition to communications through the PSTN 326.

It is also to be appreciated that the seizure detection system can be used when there is no implanted nerve stimulation device. That is, for purposes of studying seizures, it may be desirable to provide a patient with heart monitoring devices, as discussed above, and an external device of some kind to detect and transmit data regarding seizures, even in the absence of any mechanism for treating them. This approach can be suitable for some patients and desirable from a research standpoint to gather seizure information.

Figure 4:
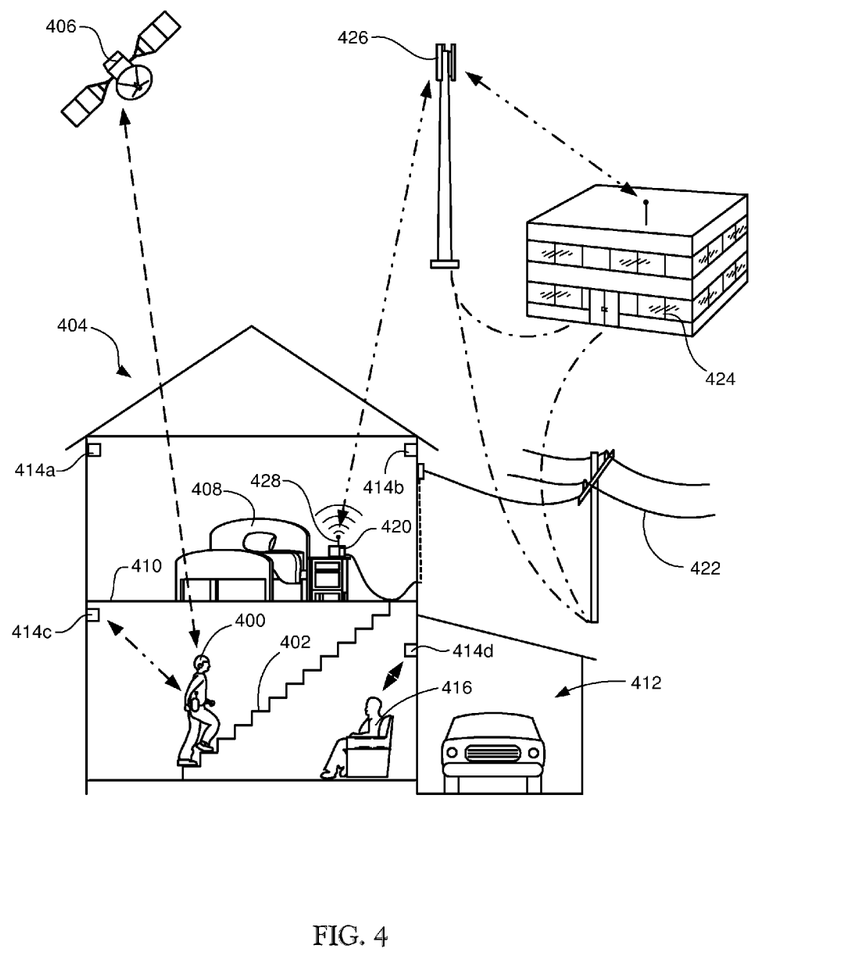
FIG. 4 is a schematic representation of another embodiment of a system for identifying a seizure episode based upon coordinate data associated with a human subject, where the coordinate data can be obtained from devices other than a GPS system.

The system can also be configured for other functions and for operation in other conditions, as shown in FIG. 4. The seizure detection system disclosed herein can incorporate stair-climbing logic to help prevent false seizure indications from exertion that results from stair climbing. For example, shown in FIG. 4 is a person 400 climbing a flight of stairs 402 in a building 404. In a situation like this, the seizure detection system can detect a pattern of velocity and altitude change that is indicative of stair-climbing. Since this sort of action is likely to raise one's heart rate, the adaptive seizure detection threshold can be reduced in a manner specific to stair-climbing. That is, since stair climbing presents a more extreme case of exertion, it is therefore more likely to induce an accelerated heart rate that is not associated with a seizure event.

The system can also incorporate neural network self-programming, so that the adaptive thresholds "learn" to match a particular patient's pattern of how speed and altitude changes result in heart rate changes. Over time, the adaptive threshold can be "trained" to follow an expected pattern of exertion versus resulting heart rate (or other autonomic) change. A seizure detection declaration is made to be more likely when the pattern of cardiac cycle deviates from the cardiac cycle that would have normally been expected given contemporary velocity data.

In addition to adjusting an adaptive heart rate threshold in conjunction with data regarding velocity or motion of the individual, the system can also use GPS positional or coordinate data to modify the seizure detection threshold based on specific coordinate locations. That is, the system can use a logical neural network self-programming and learning for recognizing specific positional patterns. For example, using data from a GPS satellite system 406, the system can logically determine that the patient is in a position of a bed 408 (e.g. on an upper floor 410 of a known residential building 404, in a substantially constant position for several continuous hours each day). If a 'bed' locational determination is made, adaptive thresholds can be adjusted to attempt to discriminate from patterns of normal sleep behaviors. Where the system determines this type of location, sudden tachycardia can be indicative either of a seizure event, or of waking and rising. To distinguish between sudden heart rate change due to a seizure and sudden heart rate change upon getting out of bed, the system can be programmed to recognize that a heart rate jump upon arising from bed is likely to occur after a change in body position. Consequently, GPS or other signals that detect body or positional changes can screen this out.

Similarly, logical determination that the patient is in a position of a car's normal patterned parking space (i.e., within a garage 412 of a residence 404) can trigger corresponding logical conclusions. If a 'car' locational determination is made, adaptive thresholds can be adjusted to 'automotive travel' mode immediately, rather than having to wait for a pattern of velocity that indicates automotive travel.

Relevant data can also be obtained from devices in addition to a GPS transceiver. For example, as shown in FIG. 2, the pulse generation device can also include an accelerometer 60 that is interconnected to the microprocessor 28. There are a wide variety of low cost, miniature accelerometers that are commercially available, and can be incorporated into an implantable device, or an external device, such a smart phone 52, wristwatch 54, etc. For example, many cardiac pacemakers currently include accelerometers to detect exercise, and can adjust pacing accordingly. Such an accelerometer device can accurately detect acceleration along three axes (up-down, forward-back, left-right), allowing the microprocessor 28 to detect the onset of motion of the patient in any direction. An inclinometer (not shown) can similarly be used to give an indication of the patient's posture, such as lying down, reclining, standing, etc. A neural network logical self-programming pattern recognition algorithm can be incorporated into the programming of the microprocessor to correlate patterns of data from the accelerometer, inclinometer, etc. with data from the GPS receiver.

As noted above, receiving GPS signals generally requires a line of sight to GPS satellites. However, there are many locations, such as inside a building, etc., where it may be difficult or impossible to obtain a GPS signal. Such a situation is suggested in FIG. 4. Correlating the accelerometer data with the most recently obtained GPS data allows adaptive threshold adjustment in the absence of a GPS signal. The accelerometer data can represent an 'activity level' in a way that is derived from the GPS data that indicates 'activity level' based on velocity changes. Thus, after a learning period of sufficient simultaneous GPS and accelerometry recording, the pattern recognition learning algorithm can have the ability to adjust seizure declaration thresholds in the absence of a GPS signal, which may be the case for many indoor locations.

Additionally, other position-finding technologies can also be used to determine location when a GPS signal is limited, such as at certain indoor locations. Other position-finding technologies that can be used can include local positioning systems, RFID systems, toll tag technologies, cell phone positional methodologies, internal radio positional networks, proximity sensors, motion sensors, and acoustic broadcasts and sensors (especially those tuned to inaudible frequencies) which can determine the location and/or motion of a patient in many locations. These types of systems can provide a local coordinate system that can provide local coordinate data regarding the position or motion of the patient. One of these types of systems is suggested in FIG. 4. It is possible that GPS detection can work within a building, as indicated by the communication line between the satellite 406 and the person 400. However, the home 404 may prevent the reception of GPS signals in many instances. Consequently, this building is equipped with a plurality of detection devices 414*a-d*, which can allow local detection of the position and motion of a patient inside the building.

These detection devices 414 can be sensors which actually sense position and/or motion (e.g. motion detectors), or they can be broadcast devices that broadcast a signal (e.g. a radio signal), and then sense reflected information. For example, the detection devices 414 can provide signals (e.g. proximity signals) to an IMD or external device upon the person of the patient, and the IMD or external device can then interpret the proximity data to independently determine the position and motion of the patient to detect the patient 400 climbing a flight of stairs 402, for example, even if the GPS system is not able to detect it. Similarly, the detection devices can detect when the person is sitting relatively still, as at 416, or in or near the bed 408. The detection devices 414 for this type of application can be cell phone positional sensors, an internal radio positional network, proximity sensors, motion sensors, or others. Thus, for example, viewing FIG. 4, detection device 414a can be a radio-frequency transmitter, detection device 414b can be a motion sensor, detection device 414c can be a proximity sensor, and detection device 414d can be an acoustic broadcast sensor.

In an interior or other location where a GPS signal may not be available, the user can 'set up' the home or commonly visited place with detection devices of two or more types. One type of detection device can be used to indicate that the area is associated with a 'high risk'. Another type of detection device can be associated with a 'low risk' location. In instances when there is only one type of detection device present, the default programming can consider decision making without the condition of 'high risk' or 'low risk' biasing the decision.

In the case of a tachycardia-based detection algorithm, one example of a high risk location can be the person's the bed 208, since tachycardia when in one's bed should be rare except in the event of an actual seizure. As another example, a bathtub (not shown) can be considered a high risk location because, even though non-seizure tachycardia could happen in the bathtub, the consequences of an unattended seizure in the bathtub carry high risk. In high risk locations the propensity to declare an event and respond can be biased toward more vigilance. On the other hand, an example of a low risk location could be a stairway 402. It is highly probable that tachycardia will be associated with exertion in a stairway. Consequently, the threshold for seizure responsive action in a stairway can be relaxed, since a tachycardia event experienced at the stairway is more likely to be due to exertion, rather than a seizure event.

The locational data that is collected when setting up the commonly visited locations can also be presented for use in patient care. For example, medical professionals, caregivers, and/or patients can analyze the patient's sleeping habits, daily rituals, frequency of exposure to 'high risk' locations, the amount of time spent in particular locations of interest, and general activity levels. These types of factors can be referred to as lifestyle factors, and can be evaluated and considered in the seizure detection system disclosed herein. For example, this data can help determine the patient's quality of life or, among other things, behavioral patterns that may lead to changes in the prescribed therapy. The conglomerated and trended positional and body sensor data may be used to collaterally quantify and communicate lifestyle factors such as in the form of standard indices like Physical Activity Level (PAL)/Physical Activity Index (PAI), Total Energy Expenditure (TEE), and other existing standards used to quantify state of health. Such indices and their trends may themselves be used to adjust a seizure detection declaration threshold, reveal trends that may be predictive of seizure propensity, or simply for presenting a measure of health improvement or decline to the healthcare provider.

An additional feature of the seizure detection system shown in FIG. 4 is a bedside monitoring unit or base station 420. This unit can operate in much the same way as other external devices disclosed above (such as the smart phone 52 in FIG. 2). It can transmit and receive low power signals with an implanted nerve stimulation device, and can receive or be programmed with GPS or other positional data. Advantageously, the bedside unit 420 can be hard-wired into a communications system, such as the PSTN, represented by wires 422, allowing rapid and reliable communications with a remote monitoring station 424 or other remote location. The base station can also include wireless capability, allowing it to communicate directly with a wireless telephone system, represented by cell tower 426, or other wireless devices. The base station and other external devices allow some device other than an implanted device to do the "heavy lifting" of communications and analysis for seizure detection, so that power demands on the implanted device are minimized.

Alternatively, in an embodiment, similar to FIG. 2, the seizure detection algorithm can be processed in either the IMD or the external device. The computational 'heavy lifting' can be performed on the external device whenever it is within range and operational, but when the external device is unavailable, the IMD can be programmed to perform the computational chores, even at the expense of battery use, so as not to lose functionality of the system as a whole.

It is to be appreciated that the system and method disclosed herein can also apply to cardiac pacemakers. That is, a pacemaker is an implantable device that can be provided with a coordinate data interface in the manner disclosed herein, and include programming to determine or adjust operational parameters based upon coordinate and/or motion data and a detected physiological condition, such as cardiac cycles.

The system and method disclosed herein can thus improve the accuracy of automated seizure detection devices and algorithms. This system has the greatest potential to improve specificity of automated seizure declarations. It can reduce battery consumption by an implanted nerve stimulation device by avoiding false alarms and incorrectly identified needs for therapy delivery. It can also reduce anxiety and disruption by avoiding false alarms for alerting-type systems. Additionally, this system and method can improve the tracking of disease progression by making seizure counts more accurate.

Although various embodiments have been shown and described, the invention is not so limited and will be understood to include all such modifications and variations as would be apparent to one skilled in the art. For example, equivalent elements may be substituted for those specifically shown and described, certain features may be used independently of other features, and the number and configuration of various vehicle components described above may be altered, all without departing from the spirit or scope of the invention as defined in the appended claims.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:
1. A system comprising:
an implantable medical device suitable for implantation into a human body;
a coordinate data interface configured to receive coordinate data for the human body;
a sensor configured to detect body signal data from the human body;
a memory configured to store the coordinate data interface and the body signal data; and activation circuitry configured to activate the implantable medical device in response to detecting an event based on the coordinate data and the body signal data.

2. The system of claim 1, wherein the coordinate data interface comprises at least one of a proximity sensor, a motion sensor, an acoustic broadcast sensor, and a radio-frequency transmitter.

3. The system of claim 1, wherein the implantable device comprises a pulse generation device for nerve stimulation, and wherein the activation circuitry comprises:
   seizure detection circuitry configured to determine at least one body parameter from the body signal data and configured to compare the at least one body parameter to a seizure threshold; and
   threshold determining circuitry to determine the seizure threshold dynamically based upon the coordinate data.

4. The system of claim 1, wherein at least one of the coordinate data interface, the sensor, and the activation circuitry are external to the human body.

5. The system of claim 4, wherein the activation circuitry is external to the human body and further comprising a communication element that includes an antenna portion configured to transmit and receive wireless communication signals between the implantable device and the activation circuitry.

6. The system of claim 1, further comprising a cellular device housing at least one of the coordinate data interface and the activation circuitry.

7. The system of claim 1, wherein the coordinate data includes global positioning system data from a global positioning system, local coordinate system data from a local coordinate system, or both.

8. The system of claim 7, wherein the coordinate data includes time data, velocity data, acceleration data, or a combination thereof.

9. The system of claim 1, wherein the memory is further configured to store movement data of the human body based on the coordinate data, wherein the event comprises a seizure event, and wherein the seizure event is detected in the human body based on the coordinate data and an amount of movement of the human body.

10. The system of claim 9, wherein the memory is further configured to log seizure event data associated with the coordinate data.

11. The system of claim 9, further comprising an antenna portion, wherein seizure event data is sent to an external communication device via the antenna.

12. The system of claim 1, wherein the memory is further configured to store input data indicating an activity being performed by the human body.

13. The system of claim 12, wherein the input data further indicates a location where the activity is being performed based on the coordinate data.

14. A system comprising:
   a medical device suitable for monitoring a patient;
   a coordinate data interface configured to receive coordinate data relative to the patient;
   a sensor configured to detect body signal data from the patient;
   a memory configured to store the coordinate data and the body signal data; and
   activation circuitry configured to activate the medical device in response to detecting an event based on the coordinate data and the body signal data.

15. The system of claim 14, wherein the coordinate data includes global positioning system data from a global positioning system, local coordinate system data from a local coordinate system, or both.

16. The system of claim 15, wherein the local coordinate system comprises at least one of a proximity sensor, a motion sensor, an acoustic broadcast sensor, and a radio-frequency transmitter.

17. The system of claim 15, wherein the coordinate data includes time data, velocity data, data, acceleration data, or a combination thereof, and wherein the activation circuitry is configured to determine whether the patient is traveling in a vehicle based on the coordinate data.

18. The system of claim 14, wherein the memory is further configured to store movement data of the patient based on the coordinate data, wherein the event comprises a seizure event, and wherein the seizure event is detected in the patient based on the coordinate data and an amount of movement of the patient.

19. The system of claim 14, wherein the medical device is configured to stimulate a nerve of the patient after being activated by the activation circuitry.

20. A method, comprising:
   monitoring a patient that has a medical device;
   receiving coordinate data relative to the patient via a coordinate data interface;
   detecting body signal data from the patient;
   storing, at a memory device, the coordinate data from the coordinate data interface and the body signal data; and
   activating the medical device in response to detecting an event based on the coordinate data and the body signal data.

* * * * *